(12) United States Patent
Sun et al.

(10) Patent No.: US 10,816,535 B2
(45) Date of Patent: Oct. 27, 2020

(54) METHOD OF ASSESSING DRYING DEPTH OF CEMENTITIOUS MATERIAL

(71) Applicant: SHENZHEN UNIVERSITY, Shenzhen, Guangdong (CN)

(72) Inventors: Hongfang Sun, Guangdong (CN); Feng Xing, Guangdong (CN); Zhili Ren, Guangdong (CN); Dawang Li, Guangdong (CN); Jian Liu, Guangdong (CN); Bing Fan, Guangdong (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 421 days.

(21) Appl. No.: 15/867,680

(22) Filed: Jan. 10, 2018

(65) Prior Publication Data

US 2018/0136188 A1    May 17, 2018

Related U.S. Application Data (63) Continuation of application No. PCT/CN2016/098752, filed on Sep. 12, 2016.

(51) Int. Cl.
| | |
|---|---|
| *G01N 33/38* | (2006.01) |
| *G01N 27/04* | (2006.01) |
| *C04B 14/06* | (2006.01) |
| *C04B 40/00* | (2006.01) |
| *G01N 1/30* | (2006.01) |

(Continued)

(52) U.S. Cl.
CPC ........... *G01N 33/383* (2013.01); *C04B 14/06* (2013.01); *C04B 40/0007* (2013.01); *G01N 1/30* (2013.01); *G01N 27/026* (2013.01); *G01N 27/04* (2013.01); *G01N 27/121* (2013.01)

(58) Field of Classification Search
CPC .. G01N 27/121; G01N 27/026; G01N 33/383; G01N 27/04; G01N 27/048; G01N 1/30; C04B 40/0007; C04B 14/06
See application file for complete search history.

(56) References Cited

U.S. PATENT DOCUMENTS

| | | | | |
|---|---|---|---|---|
| 4,293,341 A | * | 10/1981 | Dudley | ................... C04B 28/04 |
| | | | | 106/675 |
| 5,861,751 A | * | 1/1999 | Anderson | ................. G01V 3/06 |
| | | | | 324/323 |

(Continued)

FOREIGN PATENT DOCUMENTS

CN         106290485      *   1/2017   ............. G01N 27/04

*Primary Examiner* — Jeff W Natalini (57) ABSTRACT

The present invention relates to the field of material determination or analysis, and provides a method of assessing drying depth of cementitious materials including the following steps: preparing a plurality of cementitious material specimens; drying the cementitious material specimens; conducting electrochemical impedance spectrum measurement on each cementitious material specimen; accordingly determining a model for analyzing the drying depth of the cementitious material specimen. The method of assessing drying depth of the cementitious material provided by the present invention takes the influence of the resistivity changes on the model into consideration, and the drying depth of the cementitious material is reflected and reckoned with regularly changes of the electrochemical parameters, not only increasing the accuracy but also saving much testing labor, time and cost.

8 Claims, 8 Drawing Sheets

(51) Int. Cl.
*G01N 27/02* (2006.01)
*G01N 27/12* (2006.01)

(56) References Cited

U.S. PATENT DOCUMENTS

| | | | |
|---|---|---|---|
| 2014/0204405 A1* | 7/2014 | Robles Flores | H04N 1/2323 |
| | | | 358/1.14 |
| 2017/0146680 A1* | 5/2017 | Boul | G01V 3/24 |
| 2017/0284996 A1* | 10/2017 | Ghods | G01N 27/048 |
| 2019/0120707 A1* | 4/2019 | Chung | G01N 33/383 |

* cited by examiner

METHOD OF ASSESSING DRYING DEPTH OF CEMENTITIOUS MATERIAL

CROSS-REFERENCE TO RELATED APPLICATIONS

This application is a continuation application of PCT Application No. PCT/CN2016/098752 filed on Sep. 12, 2016, the entire contents of which are hereby incorporated by reference.

TECHNICAL FIELD

The present invention relates to the field of material determination or analysis, and in particular to a method of assessing the drying depth of cementitious material.

BACKGROUND

The cementitious material includes cement paste, cement mortar, cement concrete as well as reinforced concrete and cementitious products thereof. The cementitious material is the most widely used man-made building material in the world, owing to the excellent performance and relatively low cost. Most of the time, the cementitious materials are subjected to dry conditions from outer surface to inside under the influence of the external environment after being shaped. However, the drying levels and depth have essential impacts on the durability properties of the cementitious materials. For example, the surfaces of the cementitious materials being dried may result in cracking and peeling on the surfaces, thereby affecting structure durability. Therefore, it is significant to do the research on the drying depth in cementitious materials.

However, most of the traditional methods of assessing the drying depth of cementitious material are destructive approaches since the tests of the drying depth cannot be conducted unless the cementitious material is destructed. Such methods are relatively complex, requiring much labor and time, with relatively low testing efficiency and failure to realize continuous follow-up tests. In addition, some non-destructive tests are developed and conducted on the cementitious material by adopting an electrochemical impedance spectroscopy. However, such tests do not calculate the drying depth. Further, the influence of a possible change in the resistivity inside a cementitious material specimen on a model for analyzing impedance spectrum is not taken into consideration since the cementitious material is considered as an electrically uniform system.

SUMMARY

The technical problem to be solved by the present invention is to provide a method of assessing drying depth of cementitious material aimed at testing the drying depth of the cementitious material meanwhile considering the influence of the resistivity change on a model to analyze impedance spectra.

The present invention is implemented as follows. A method of assessing drying depth of cementitious material includes the following steps:
preparing a plurality of cementitious material specimens;
drying the cementitious material specimens;
conducting electrochemical impedance spectroscopy measurement on each cementitious material specimen; and
accordingly determining a model for analyzing the drying depth of the cementitious material specimen;

wherein, the step of determining a model for analyzing the drying depth of the cementitious material includes: dividing the cementitious material specimen into three parts including, from an outer surface of the specimen, a first part with resistivity rising caused by soaked filter paper and drying (drying influenced), a second part with resistivity decreasing caused by soaked filter paper and drying (drying influenced), and a third part not influenced by drying, wherein the first part and the second part are collectively a drying influenced part; dividing the drying influenced part into n elements, in which the first k elements denoted by 1 belongs to the first part, and the following (n−k) elements denoted by 2, from the (k+1)th element to the nth element, belong to the second part, and the third part is denoted by δ; wherein, $t_1$ represents the depth of the first part of the cementitious material specimen, $t_2$ is considered to be drying influenced depth of the cementitious material specimen; γ is a constant indicating how sharply the resistivity varies.

wherein, $\rho_0$ is the resistivity of the outer surface of the cementitious material specimen, $\rho_\delta$ is the resistivity of the third part not influenced by drying, $\rho_1(t)$ is the resistivity of the first part of the specimen at a drying depth of t, and $\rho_2(t)$ is the resistivity of the second part at a drying depth of t; then $\rho_1(t)$ and $\rho_2(t)$ are derived from the following equations, respectively:

$$\rho_1(t) = \rho_\delta \left[ \frac{\rho_\delta}{\rho_0} + \left(1 - \frac{\rho_\delta}{\rho_0}\right)\xi_1^\gamma \right]^{-1}, 0 < t \leq t_1;$$

$$\rho_2(t) = \rho_\delta \left[ \frac{\rho_\delta}{\rho_0} + \left(1 - \frac{\rho_\delta}{\rho_0}\right)\xi_2^\gamma \right]^{-1}, t_1 < t \leq t_2;$$

in which $$\xi_1 = \frac{2t_1 - t}{t_2}, \xi_2 = \frac{t}{t_2}.$$

Preferably, the model for analyzing the drying depth of the cementitious material includes the following equation:

$$Z = 2 \sum_{i=1}^{k} \frac{\frac{\rho_1(t_i)t_i}{S}}{1 + [2\pi f \varepsilon_0 \varepsilon \rho_1(t_i)]j} + 2 \sum_{i=k+1}^{n} \frac{\frac{\rho_2(t_i)t_i}{S}}{1 + [2\pi f \varepsilon_0 \varepsilon \rho_2(t_i)]j} + \frac{\frac{\rho_\delta(l/2 - t_2)}{S}}{1 + [2\pi f \varepsilon_0 \varepsilon \rho_\delta]j};$$

where Z is an impedance of the entire cementitious material specimen related to frequency; ε is a permittivity of vacuum; ε is a relative dielectric constant of the cementitious material specimen; π is the mathematic constant defined as the ratio of circumference to its diameter, S is a cross sectional area of the cementitious material specimen, l is a length of the cementitious material specimen, and j is an imaginary unit.

Preferably, the step of preparing the cementitious material specimen includes:
preparing a cubical cementitious material specimen having a dimension of 30×30×30 mm$^3$, a water-to-cement ratio of 0.4, and a mass ratio of cement to sand of 1:1, curing the cementitious material specimen at a temperature of 20±2° C.

with a relative humidity greater than 95% for a desired age, to obtain the cementitious material specimen for testing.

Preferably, the sand is ISO standard sand.

Preferably, the desired age is 7 days, 14 days or 28 days.

Preferably, the step of drying the cementitious material specimens includes:

sealing four sides of the cementitious material specimen with wax, drying the cementitious material specimen for 1, 4, 24 or 48 hours at a constant temperature of 50° C., respectively, and placing the specimen in between two electrodes for conducting the electrochemical impedance spectroscopy measurement on each specimen.

Preferably, the step of drying the cementitious material specimens includes:

ethanol-pretreated drying: soaking the cementitious material specimen in ethanol for 24 hours, and then refreshing the ethanol to soak the cementitious material specimens for another 24 hours to stop the hydration of the cementitious material specimens; sealing four sides of the cementitious material specimen with wax, drying the specimens for 1, 4, 24 or 48 hours at a constant temperature of 50° C. respectively, and conducting the electrochemical impedance spectroscopy measurement on each specimen.

Preferably, the step of conducting electrochemical impedance spectrocopy measurement includes:

setting EIS parameter with an AC signal as a sine-wave current of 10 mA, and a measuring frequency range of 0.1 Hz~1 MHz;

preparing two electrodes for measuring: preparing two pieces of filter paper each with a size of 30×30 mm$^2$, soaking each filter paper with 1 ml saturated calcium hydroxide solution, the two pieces of filter paper being applied to opposite unsealed ends of the cementitious material specimen respectively with each piece of filter paper being sandwiched between the cementitious material specimen and a steel plate, and connecting the steel plates to an electrochemical work station to conduct the measurement.

Compared with the prior art, the embodiment of the present invention has the advantages that the method of assessing the drying depth of cementitious material provided by the embodiment of the present invention takes the influence of the resistivity change on the model into consideration, and the drying depth of the cementitious material is derived from the change of the electrochemical parameters, not only increasing the accuracy but also saving much labor, time and cost for testing compared with the existing testing methods. The electrochemical impedance spectrum method provided by the present invention can efficiently reflect the microstructure of the cementitious material specimen. The electrochemical impedance spectroscopy approach is high sensitive, spending less time for testing, and is a non-destructive detecting approach, thereby being a rapid and efficient approach for measuring the drying depth of the cementitious material.

DESCRIPTION OF THE EMBODIMENTS

In order to clarify the object, technical solution and advantages of the present invention to a greater extent, the present invention will be further explained in detail in conjunction to drawings and embodiments. It is understood that the specific embodiments described herein are only used for explaining the present invention, but not to limit the present invention.

The present invention is implemented as follows. A method of assessing drying depth of cementitious material includes the following steps:

preparing a plurality of cementitious material specimens;

drying the cementitious material specimens;

conducting electrochemical impedance spectroscopy (EIS) measurement on each cementitious material specimen; and accordingly determining a model for analyzing the drying depth of the cementitious material specimen;

wherein, the step of determining a model for analyzing the drying depth of the cementitious material includes: dividing the cementitious material specimen into three parts including, from an outer surface of the specimen, a first part with resistivity rising caused by soaked filter paper and drying (drying influenced), a second part with resistivity decreasing caused by soaked filter paper and drying (drying influenced), and a third part not influenced by drying, wherein the first part and the second part are collectively called as drying influenced part; dividing the drying influenced part into n elements, in which the first k elements denoted by 1 belongs to the first part, and the following (n−k) elements denoted by 2, from the (k+1)th element to the nth element, belong to the second part, and the third part is denoted by δ; wherein, $t_1$ represents the depth of the first part of the cementitious material specimen, $t_2$ is considered to be drying influenced depth of the cementitious material specimen; γ is a constant indicating how sharply the resistivity varies.

Let $\rho_0$ be the resistivity of the outer surface of the cementitious material specimen, $\rho_\delta$ be the resistivity of the third part not influenced by drying, $\rho_1(t)$ be the resistivity of the first part of the specimen at a drying depth of t, and $\rho_2(t)$ be the resistivity of the second part at a drying depth of t; then $\rho_1(t)$ and $\rho_2(t)$ can be derived from the following equations, respectively:

$$\rho_1(t) = \rho_\delta \left[\frac{\rho_\delta}{\rho_0} + \left(1 - \frac{\rho_\delta}{\rho_0}\right)\xi_1^\gamma\right]^{-1}, 0 < t \leq t_1;$$

$$\rho_2(t) = \rho_\delta \left[\frac{\rho_\delta}{\rho_0} + \left(1 - \frac{\rho_\delta}{\rho_0}\right)\xi_2^\gamma\right]^{-1}, t_1 < t \leq t_2;$$

in which $$\xi_1 = \frac{2t_1 - t}{t_2}, \xi_2 = \frac{t}{t_2}.$$

Specifically, the model for analyzing the drying depth of the cementitious material includes the following equation:

$$Z = 2\sum_{i=1}^{k} \frac{\frac{\rho_1(t_i)t_i}{S}}{1 + [2\pi f \varepsilon_0 \varepsilon \rho_1(t_i)]j} + 2\sum_{i=k+1}^{n} \frac{\frac{\rho_2(t_i)t_i}{S}}{1 + [2\pi f \varepsilon_0 \varepsilon \rho_2(t_i)]j} + \frac{\frac{\rho_\delta(l/2 - t_2)}{S}}{1 + [2\pi f \varepsilon_0 \varepsilon \rho_\delta]j};$$

where Z is an impedance of the entire cementitious material specimen related to frequency; $\varepsilon_0$ is a permittivity of vacuum; ε is a relative dielectric constant of the cementitious material specimen; π is the mathematic constant defined as the ratio of circumference to its diameter, S is a cross sectional area of the cementitious material specimen, l is a length of the cementitious material specimen, and j is an imaginary unit.

The method of assessing the drying depth of cementitious material provided by the embodiment of the present invention takes the influence of the resistivity change on the model into consideration, and the drying depth of the cementitious material is derived from the change of the electrochemical parameters, not only increasing the accuracy but also saving much labor, time and cost for testing compared with the existing testing methods. The electrochemical impedance spectrum method provided by the present invention can efficiently reflect the microstructure of the cementitious material specimen. The electrochemical impedance spectroscopy approach is high sensitive, spending less time for testing, and is a non-destructive detecting approach, thereby being a rapid and efficient approach for measuring the drying depth of the cementitious material.

Preferably, the step of preparing the cementitious material specimen includes: preparing a cubical cementitious material specimen having a dimension of 30×30×30 mm³, a water-to-cement ratio of 0.4, and a mass ratio of cement to sand of 1:1, curing the cementitious material specimen at a temperature of 20±2° C. with a relative humidity greater than 95% for a desired age, to obtain the cementitious material specimen for testing.

The cement is P.O. 42.5 ordinary Portland cement produced by Huarun Cement plant (Guangdong, China). Deionized water is used. The sand is ISO standard sand manufactured by Xiamen ISO Standard Sand Co., Ltd.

Specifically, the step of drying the cementitious material specimen includes:

sealing four sides of the cementitious material specimen with wax, drying the cementitious material specimen for 1, 4, 24 or 48 hours at a constant temperature of 50° C., respectively, and placing the specimen in between two electrodes for conducting the electrochemical impedance spectroscopy test.

Specifically, the step of drying the cementitious material specimen can also be conducted as ethanol-pretreated drying:

ethanol-pretreated drying: soaking the cementitious material specimen in ethanol for 24 hours, and then refreshing the ethanol to soak the cementitious material specimens for another 24 hours to stop the hydration of the cementitious material specimens; sealing four sides of the cementitious material specimen with wax, drying the specimens for 1, 4, 24 or 48 hours at a constant temperature of 50° C. respectively, and conducting the electrochemical impedance spectroscopy test on the specimens.

Specifically, the testing ages include 7, 14, or 28 days. By comparison, the drying depths of cement mortar at different ages but with the same drying durations can be investigated.

Figure 1:
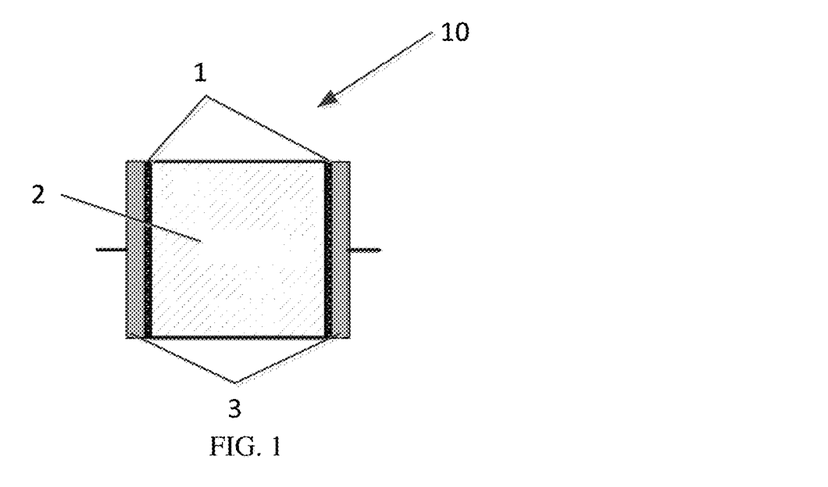
FIG. 1 is a schematic view of two-electrode arrangement for measurement according to an embodiment of the present invention.

Further, the step of conducting electrochemical impedance spectrocopy measurement includes:

setting EIS parameter with an AC signal as a sine-wave current of 10 mA, and a measuring frequency range of 1 kHz-1 MHz;

preparing two electrodes for measuring: preparing two pieces of filter paper each with a size of 30×30 mm², soaking each filter paper with 1 ml saturated calcium hydroxide solution, as shown in FIG. 1, the two pieces of filter paper 1 being applied to opposite unsealed ends of the cementitious material specimen 2 respectively and being sandwiched between the cementitious material specimen and a steel plate 3, to form a conducting electrode 10, and connecting the steel plate 3 to an electrochemical work station to conduct a measurement.

Figure 2A:
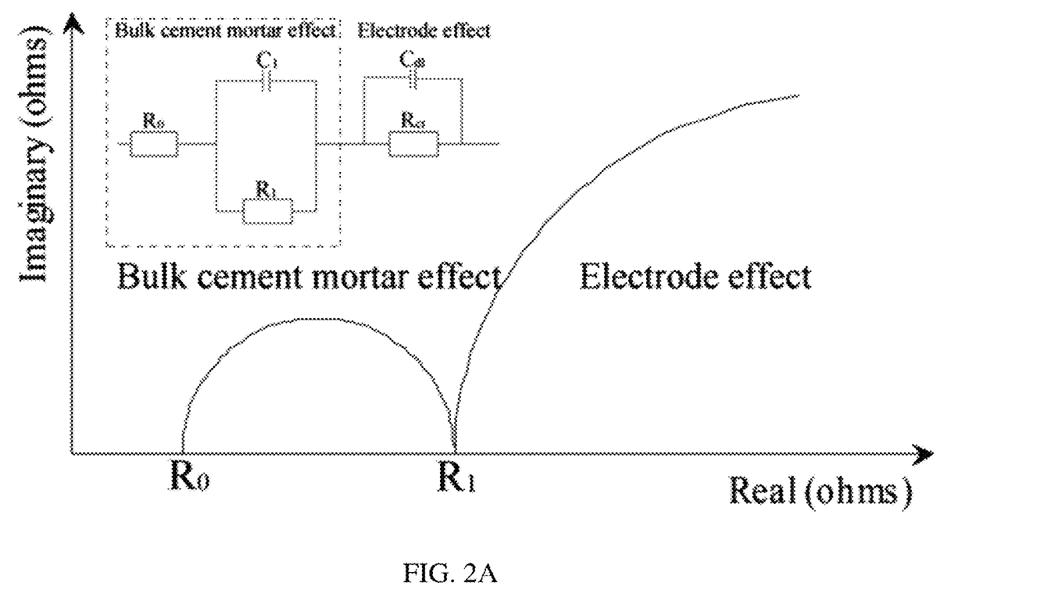
FIG. 2A is a schematic diagram of impedance spectrum obtained for the cementitious material specimen with conventional electrical equivalent circuit.
Figure 2B:
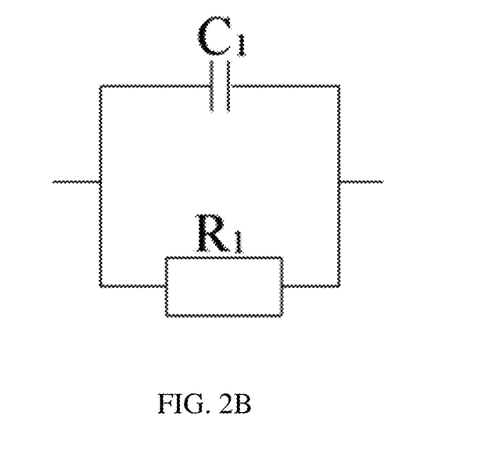
FIG. 2B is a schematic diagram of a simplified conventional electrical equivalent circuit.

As for the homogeneous cementitious material sample, its equivalent circuit shown in FIG. 2A can be used to represent the model, wherein $R_0$, $R_1$, $C_1$ represent a high-frequency resistance, a solid-liquid interface resistance and a capacitance, respectively, and $R_{ct}$ and $C_{dl}$ represent a cement-electrode interface charge transfer resistance and a double layer capacitance respectively. As for $R_0$, the literatures show that the electrochemical impedance spectroscopy of the cementitious specimen is basically intersected with a real axis at the point of 0, so $R_0$ can be neglected. $R_{ct}$ and $C_{dl}$ correspond to low frequency impedance arcs in the Nyquist plot and are physical quantities related to the property of the electrode. $R_{ct}$ is a straight line when it is great enough. Since the properties of the cement mortar itself are mainly studied herein, $R_{ct}$ and $C_{dl}$ cannot be considered either. Based on the situations in this research, the model in FIG. 2A can be represented by simplified circuit shown in FIG. 2B.

Figure 2C:
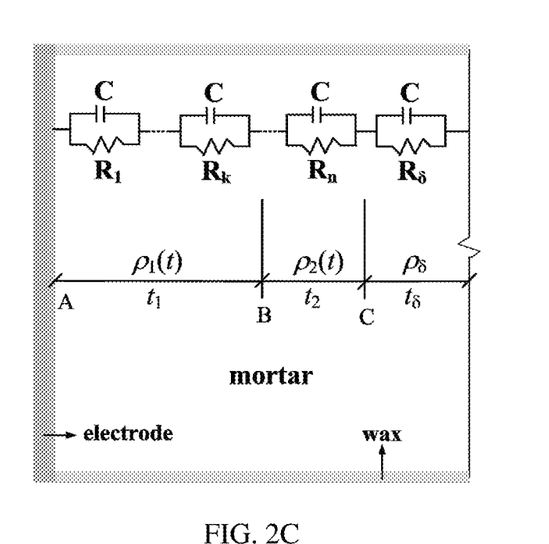
FIG. 2C is equivalent circuit for drying influenced cementitious material specimen according to the embodiment of the present invention.

Referring to FIG. 2C, according to the present invention, for cement mortar with varied resistivity, the equivalent circuit can be divided into three parts. From an outer surface of the specimen, a first part with resistivity rising ($\rho 1(t)$) caused by soaked filter paper and drying (drying influenced, and is divided into k elements), a second part with resistivity decreasing ($\rho 2(t)$) caused by soaked filter paper and drying (drying influenced), and a third part not influenced by drying, wherein the first two parts are collectively called as drying influenced part and is divided into n elements of (RiC). Finally, the third part which is not influenced by drying has a constant resistivity $\rho\delta$ and can be described by one element (R$\delta$C). The impedance expression for the entire cement mortar can be written as $$Z(\omega) = \sum_{i=1}^{k} \frac{R_i}{1+j\omega\tau_i} + \sum_{i=k+1}^{n} \frac{R_i}{1+j\omega\tau_i} + \frac{R_\delta}{1+j\omega\tau_\delta}.$$

where $\tau_i = R_i C$ is time constant.

Discretizing and substituting $$R = \frac{\rho l}{S} \text{ and } C = \frac{\varepsilon_0 \varepsilon S}{d},$$

the impedance can be expressed as $$Z(\omega) = \sum_{i=1}^{k} \frac{\frac{\rho_1(t_i)t_i}{S}}{1+j\omega\varepsilon_0\varepsilon\rho_1(t_i)} + \sum_{i=k+1}^{n} \frac{\frac{\rho_2(t_i)t_i}{S}}{1+j\omega\varepsilon_0\varepsilon\rho_2(t_i)} + \frac{\frac{\rho_\delta(l-t_2)}{S}}{1+j\omega\varepsilon_0\varepsilon\rho_\delta}$$

where $t_i$ is the thickness of the ith element, $\varepsilon_0$ is the permittivity of vacuum, $\varepsilon$ is the dielectric constant of cement mortar while S and l are the cross-sectional area and length of mortar.

By fitting the measured impedance spectra using the above equation, the resistivity distribution as well as the drying depth $t_2$ can be obtained. The above model for calculation of impedance of cement mortar would be used to fit impedance curves in the subsequent section.

Figure 3:
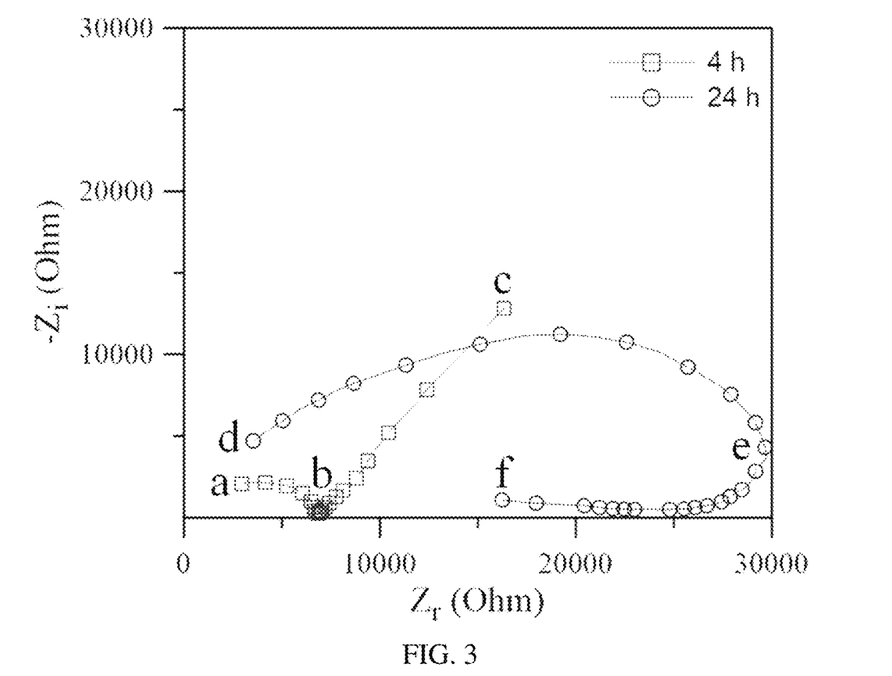
FIG. 3 shows Nyquist plots for 4 and 24 hours respectively directly dried cementitious material specimens according to the embodiment of the present invention.

For the impedance spectra of the dried cementitious material specimens, taking the specimens dried for 4 hours and 24 hours as examples, their impedance spectra are shown in FIG. 3. In lower frequency region, a straight line (bc in FIG. 3) is observed for 4 hours dried cementitious material specimen which is mainly caused by the resistance and double-layer capacitance of the contact surfaces between the electrode and the cementitious material specimen rather than the bulk specimen itself. However, for the spectrum of the specimen dried for 24 hours, a pseudo-inductance arc (ef segment in FIG. 3) is observed at the lower frequency region which is caused by the influence of contact with electrode. Therefore, during the analysis of the impedance spectrum, the part below 1 kHz is neglected, and only the part with the frequency band between 1 kHz-1 MHz reflecting the specimen properties is fitted. In addition, it is found that the impedance spectrum at high-frequency band presents significant asymmetry which increases with the prolonged drying time. This is different from a symmetrical impedance spectrum obtained under the water-saturated condition. This also suggests there will be a considerable deviation when the conventional model is adopted for fitting since it can only provide a symmetrical fitting.

Figure 4:
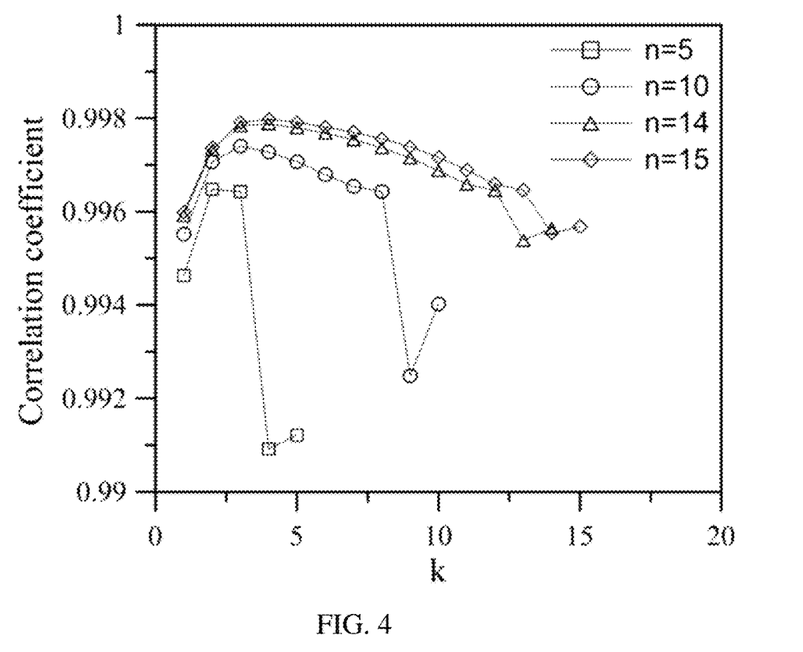
FIG. 4 is a schematic diagram of a correlation coefficient at various k and n values for the cementitious material specimen dried for 24 hours according to the embodiment of the present invention.

When the model for impedance spectrum measurement provided by the present embodiment is used to fit the impedance spectrum, the values of k and n (step size) should be determined, to not only ensure the good fitting, but also to be appropriate for the limited measuring data to ensure the accuracy of solutions of equations. In order to evaluate the fitting efficacy, the correlation coefficient is introduced. The closer to 1 the correlation coefficient is, the better the curve fitting is; the closer to 0, the worse the curve fitting is. Taking the fitting of the impedance spectrum of the cementitious material dried for 24 hours as an example, the relation of the correlation coefficient of the curve and values of k and n is shown in FIG. 4, and it is shown that when the value of n is smaller, the fitting efficacy is worse since the separated layer of the cementitious material specimen is not thin enough, which leads to relatively great deviation. With the increase in value of n, the correlation coefficient increases continually. However, when n reaches 14 and 15, the velocity of increase of the correlation coefficient slows down, and the highest points are basically overlapped. If the value of n continuously increases, the correlation coefficient does not increase significantly, but increase the calculation burden. Therefore, for the sample dried for 24 hours, the value of n is 15. As for the variation in the value of k, it is seen that with the increase in the value of k, the correlation coefficient increases firstly and then decreases. When k=4, the correlation coefficient is closest to 1, which shows that the fitting efficacy is the best, so k is 4. In a word, when the model of the present invention is used to fit the electrochemical impedance of the cementitious material specimen directly dried for 24 hours, the value of k=4 and n=15 is the best choice. The same procedure is adopted for other specimens dried for different period of time to determine the values of k and n.

Figure 5:
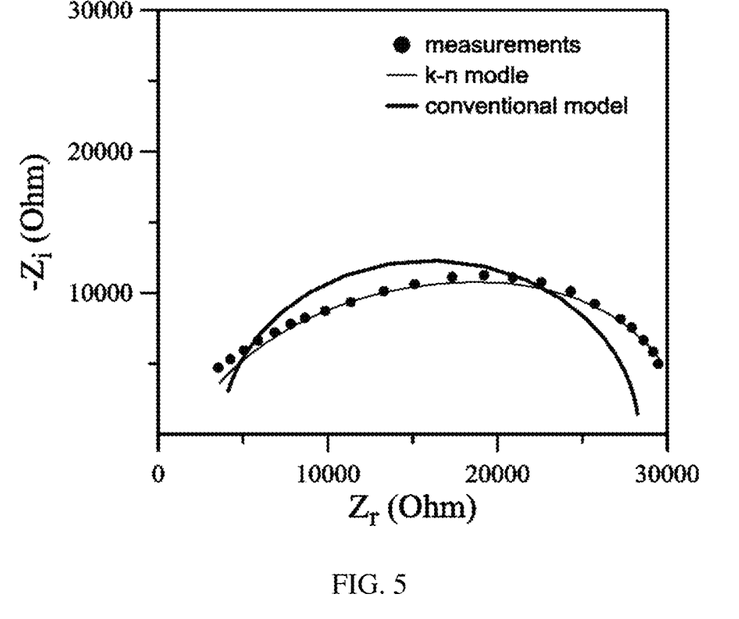
FIG. 5 shows curve fitting comparison between the model according to the embodiment of the present invention and the model according to the conventional model to the measuring data.

Taking the impedance spectrum of the specimen directly dried for 24 hours as an example, the accuracy of the mathematical model for testing is verified. The fitting curve of the model for testing according to the embodiment of the present invention is compared with that of the convention model, and the result is shown in FIG. 5. The cementitious material specimen mainly includes the components of cement gel, aggregate and pore solution, wherein, the cement gel and the aggregate are considered as electrically insulators, hence the only conductive path is through the pore solution. It can be seen from FIG. 5 that the asymmetric spectrum can be much better fitted by the model of the present invention than the conventional model. Therefore, it accounts for the fact that the model provided by the present embodiment has better fitting to the impedance spectrum with a resistivity change of the cementitious material specimen caused by being dried from outer surface to inside.

Drying of the specimen can be direct drying and ethanol-pretreated drying.

Figure 6:
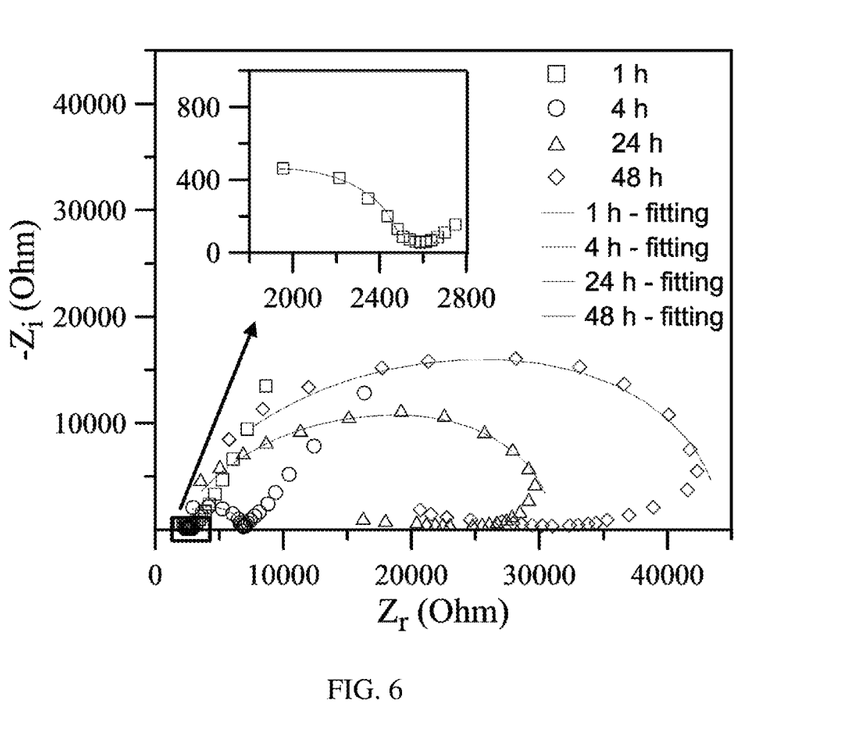
FIG. 6 shows a schematic diagram of Nyquist curves obtained by measurement on the cementitious material specimens dried for different time and a fitting efficacy according to the embodiment of the present invention.

As for direct drying, the cementitious material specimens cured for 28 days are dried for 1, 4, 24 and 48 hours respectively, and the obtained impedance spectrum are as shown in FIG. 6. It can be seen from FIG. 6 that with the prolonged drying time, the radius of a capacitance arc increases, indicating that the resistance is increased. This is caused by a loss of the pore solution in the mortar due to evaporation. The pseudo-inductance arc at the low frequency segment appears after 4 hours of drying, but this part is not related to the specimen property. So this part is not within the scope of analysis.

Figure 7:
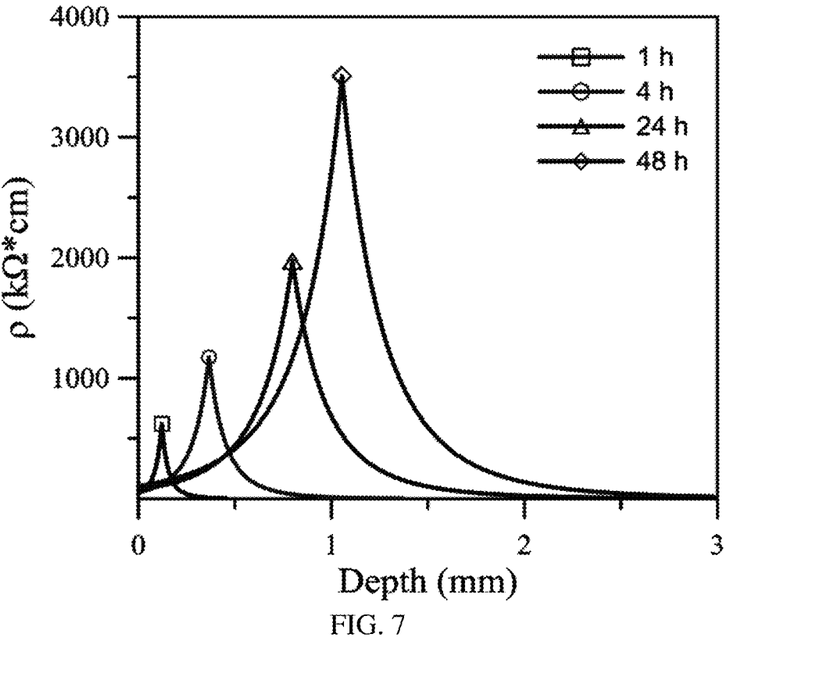
FIG. 7 shows curves of the resistivity of the cementitious material specimens directly dried for different time varying over the depth according to the embodiment of the present invention.
Figure 8:
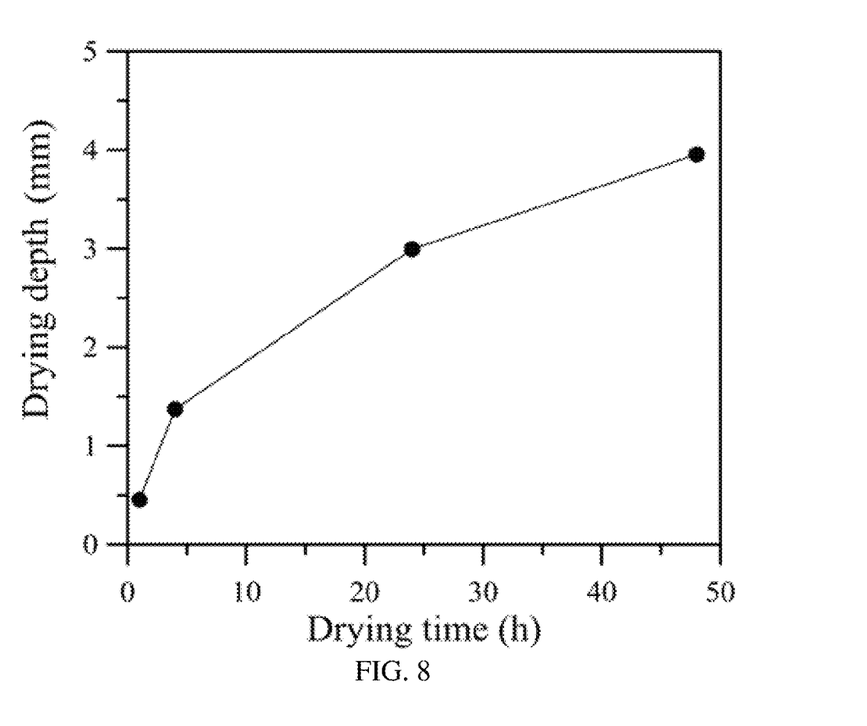
FIG. 8 shows a curve of the drying depth of the cementitious material sample varying over drying time according to the embodiment of the present invention.

Table 1 shows parameters derived by fitting the cementitious material specimens dried for different time with the model, and the correlation coefficients according to Table 1 are all close to 1. which can be seen that k–n model fits well for all the drying time (the correlation coefficient as seen in Table 1). In addition, the values of $\rho_\delta$, $\rho_{r1}$, and $t_2$ are extracted and listed in Table 1, and the distribution of the resistivity p along the depth of the cementitious material specimen is plotted in FIG. 7. The influence of drying time on drying depth $t_2$ is shown in FIG. 8.

It can be found that even for the cementitious material specimens of the same batch, there are certain differences in the value of $\rho_\delta$ (the resistivity of the area not influenced by drying) which are in a range of 3-5 k$\Omega$*cm. This is due to the fact that the cementitious material specimen itself is a complicated mixture, and the internal components and pore distribution being not uniform in the entire individual. Therefore, it is basically supposed that the value of the resistivity of the cementitious material specimen is usually within this range when the cementitious material sample is not dried. The value of $\rho_{r1}$ represents the maximum value of the resistivity in the entire specimen tested. With the increase in the drying time, $\rho_{r1}$ monotonously increases, and the depth of the maximum value $\rho_{r1}$ increases accordingly, which suggests that the cementitious material specimen is getting 'dryer', and the deeper part is affected by drying with time.

TABLE 1

| Drying time (h) | $\rho_\delta$ (k$\Omega$*cm) | $\rho_{r1}$ (k$\Omega$*cm) | Drying depth (mm) | Correlation coefficient |
|---|---|---|---|---|
| 1 | 4.17 | 628 | 0.45 | 0.994 |
| 4 | 3.47 | 1174 | 1.37 | 0.997 |
| 24 | 3.95 | 1974 | 2.99 | 0.998 |
| 48 | 4.40 | 3507 | 3.96 | 0.997 |

As for the drying depth, the drying depth over the drying time is shown in FIG. 8 and Table 1. It can be seen that the drying durations prolongs to 48 hours from 1 hour, the drying depth increases from 0.45 mm to 3.96 mm, since with the increase in the drying time, more and deeper pore solution of the cementitious material specimen runs out through open pores, such that the drying depth increases. It can also been seen that with increasing depth, the rating of drying was lower. This is due to the reason that with the increase in the drying depth, it is difficult for the pore water to evaporate from pores because of the tortuosity of the pore structure; on the other hand, evaporation of water during drying results in slight shrinkage of pore size, which in turn make it difficult for the water to evaporate.

Figure 9:
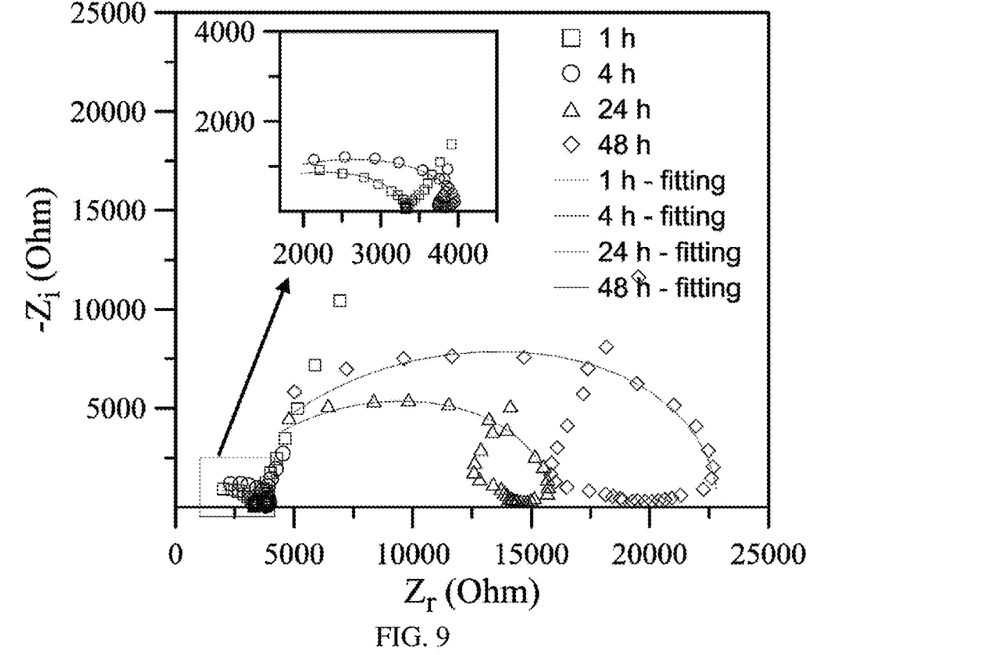
FIG. 9 shows Nyquist curves obtained by measurement on the cementitious material specimens subjected to ethanol-pretreated drying at different drying time and the fitting efficacy according to the embodiment of the present invention.
Figure 10:
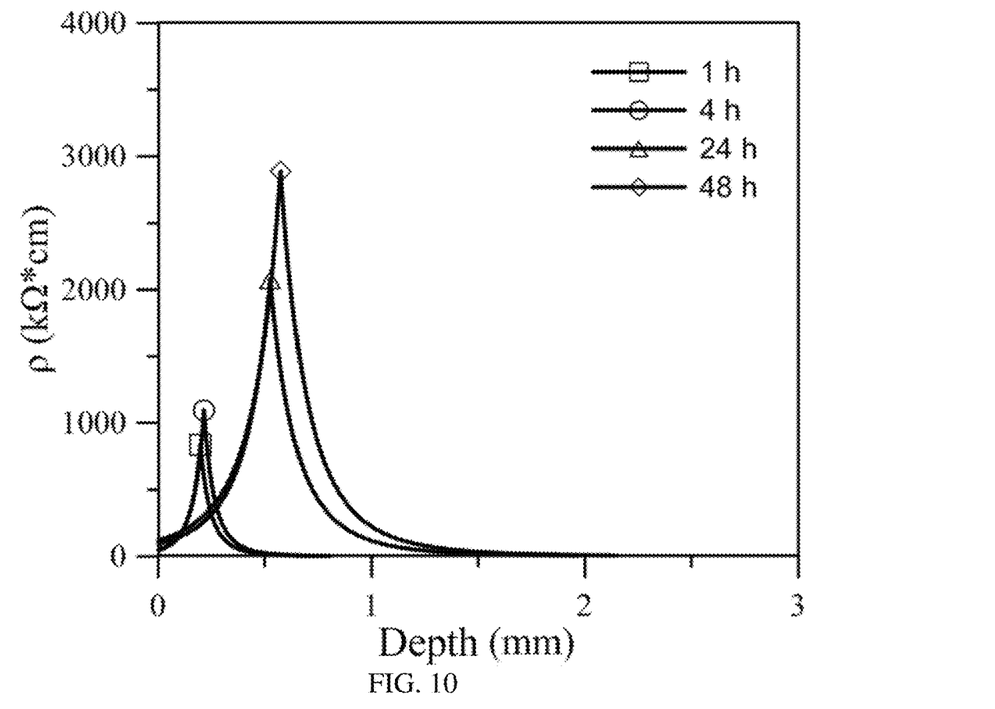
FIG. 10 shows a curve of the resistivity of the cementitious material specimens soaked in ethanol and dried for different time varying over the depth according to the embodiment of the present invention.
Figure 11:
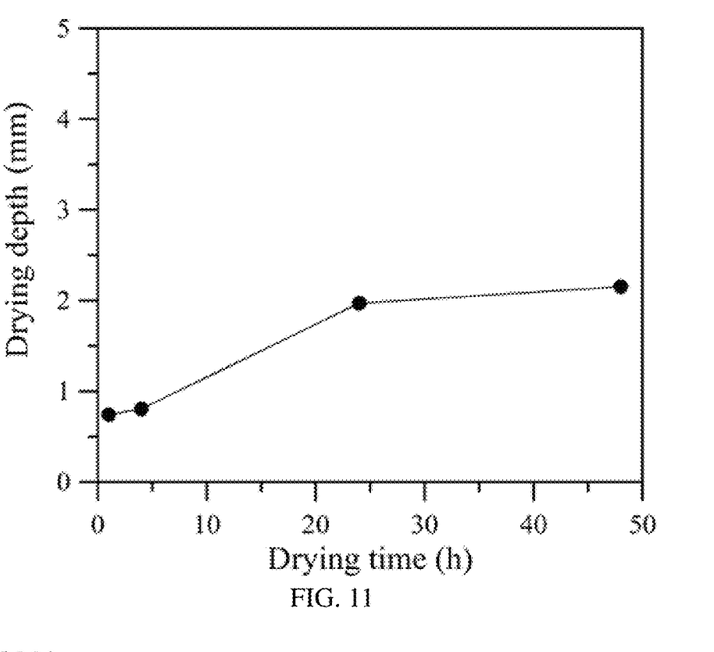
FIG. 11 is a schematic diagram showing the drying depth of the cementitious material specimen soaked in ethanol varying over drying time according to the embodiment of the present invention.

As for the ethanol-pretreated drying, the specimens cured by the ethanol pretreatment are dried for 1, 4, 24 and 48 hours respectively, and the obtained impedance spectrograms are shown in FIG. 9. The obtained result has a trend similar to that of the direct drying, but straight line as well as the pseudo-inductive loops is observed at low frequency. However, this part is also related to the electrode, so this part is not discussed emphatically here. The capacitance arc part in FIG. 9 is fitted by using this model, and the fitting curve is shown in FIG. 9 which also has good fitting efficacy. Table 2 shows the parameters obtained by fitting the cementitious material specimen soaked into ethanol and dried for different times by using the model. The resistivity p over the depth of the cementitious material specimens is shown in FIG. 10, and the curve of the drying depth $t_2$ over the drying time is shown in FIG. 11.

$\rho_\delta$ of the cementitious material specimen soaked in ethanol is ranged between 3-7 k$\Omega$*cm, which is basically the same as that of the sample directly dried. It can be seen from FIG. 11 and Table 2 that with the increase in the drying time, the drying depth is increased from 0.74 mm to 2.15 mm, but the drying depth value after ethanol pretreatment is less than that of direct drying. This is due to the fact that the ethanol-pretreating reduces the influence level of cement hydration at a high temperature to the greatest extent.

TABLE 2

| Drying time (h) | $\rho_\delta$ (k$\Omega$*cm) | $\rho_{r1}$ (k$\Omega$*cm) | Drying depth (mm) | Correlation coefficient |
|---|---|---|---|---|
| 1 | 3.22 | 839 | 0.74 | 0.996 |
| 4 | 3.00 | 1093 | 0.81 | 0.999 |
| 24 | 5.65 | 2077 | 1.97 | 0.996 |
| 48 | 6.56 | 2886 | 2.15 | 0.993 |

Figure 12:
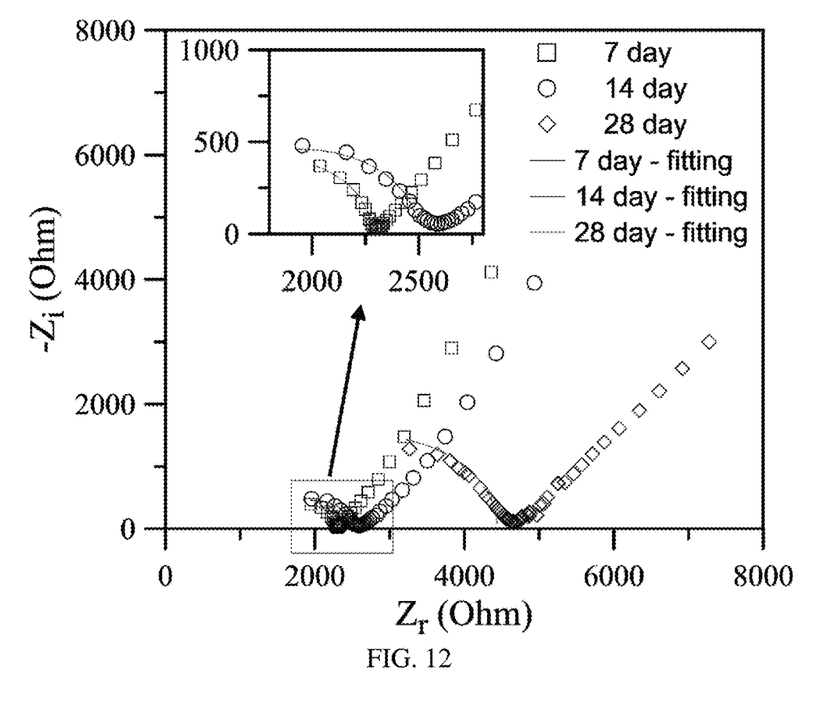
FIG. 12 shows Nyquist curves obtained by measurement on the cementitious material specimens hydrated for different ages and the fitting efficacy according to the embodiment of the present invention.
Figure 13:
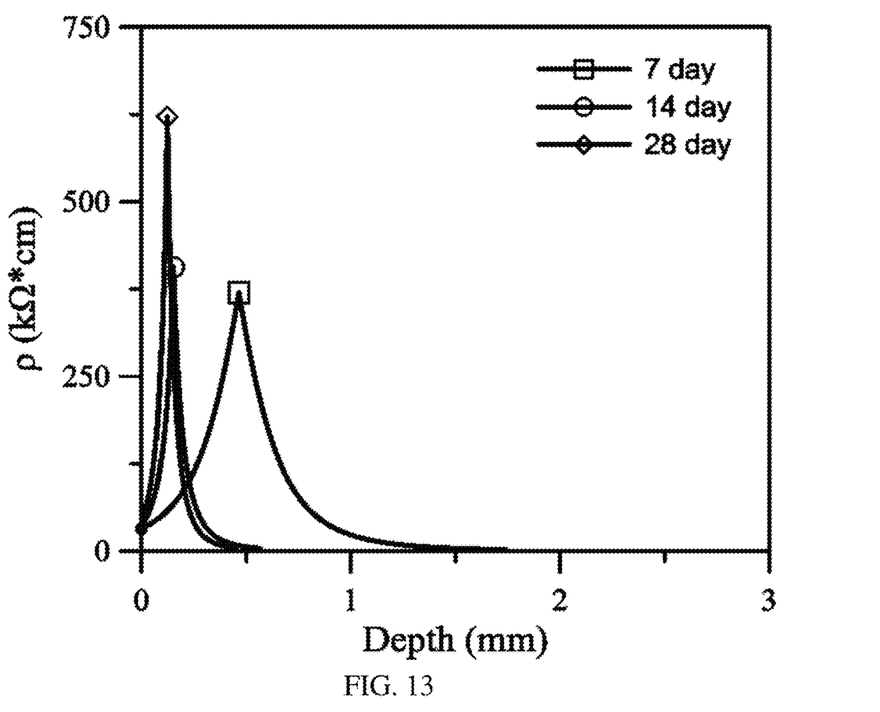
FIG. 13 shows a curve of the resistivity of the ethanol-pretreated cementitious material specimens at different ages varying over the depth provided by the embodiment of the present invention.
Figure 14:
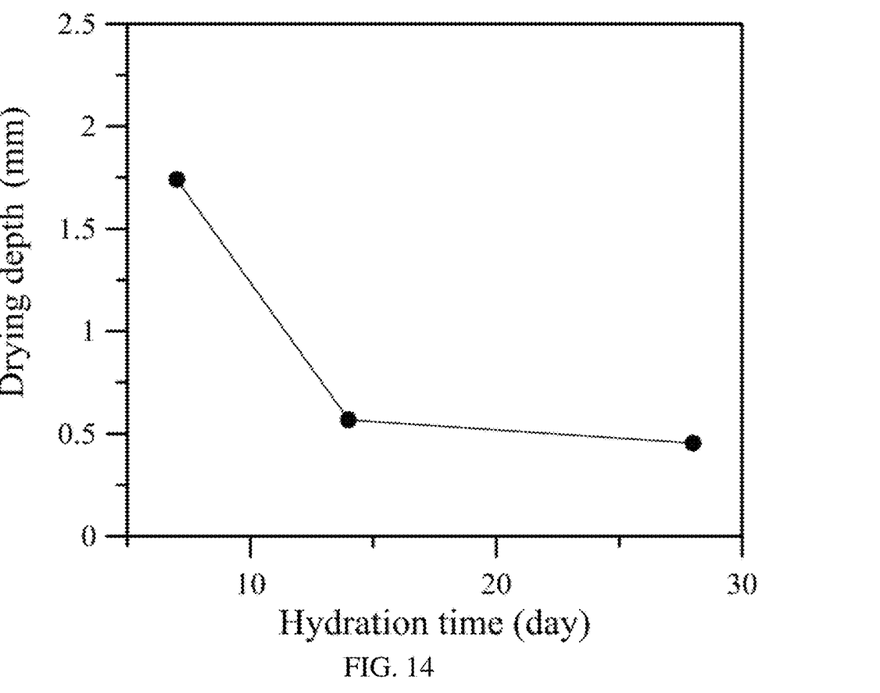
FIG. 14 shows the drying depths of the cementitious material specimens at different ages dried for 1 hour with ethanol-pretreating according to the embodiment of the present invention.

The cementitious material specimens are cured for 7, 14 and 28 days in a water-saturated state, and then dried for 1 hour. The measured impedance spectrum is shown in FIG. 12, and the fitting result obtained by using this model is as shown in FIG. 12 and Table 3. Table 3 shows the parameters obtained by fitting the spectra of cement mortar cementitious material specimen at different ages by using this model. The resistivity of the cementitious material specimen over the depth of the cementitious material specimen is shown in FIG. 13, and the drying depth over the age is shown in FIG. 14. From Table 3, it can be seen that $\rho_\delta$ monotonously increases with the increase in age, increasing from 2.03 k$\Omega$*cm of 7 days to 3.96 k$\Omega$*cm of 14 days and to 4.17 k$\Omega$*cm of 28 days, respectively. This is because with the increase of the age, the pore structure of the cement mortar is increasingly dense, which caused the increase of the hydration level of the cement. Moreover, the peak value of $\rho_{r1}$ of the resistivity also increases with age from 370 k$\Omega$*cm of 7 days to 407 k$\Omega$*cm of 14 days and to 628 k$\Omega$*cm of 28 days for the same reason as above.

From FIG. 13, it can be obviously seen that with the increase in age, the resistivity curve is increasingly steep, but the influenced depth becomes less. This is because at early age, the hydration degree of the cementitious material specimen is relatively low, the pores inside the cementitious material specimen are relatively large, and the cementitious material specimen is easily dried; whereas at late age, the pores become small, even becomes closed, such that the cementitious material specimen is difficultly to be dried. Only the pore water at the external layer can be dried, so the drying depth is reduced.

TABLE 3

| age (天) | $\rho_\delta$ (kΩ*cm) | $\rho_{t1}$ (kΩ*cm) | Drying depth (mm) | Correlation coefficient |
|---|---|---|---|---|
| 7 | 2.03 | 370 | 1.74 | 0.984 |
| 14 | 3.96 | 407 | 0.57 | 0.990 |
| 28 | 4.17 | 628 | 0.45 | 0.994 |

From FIG. 14, it can be seen that after the specimen is dried for 1 hour, the drying depth of the specimen becomes 0.57 mm of 14 days and 0.45 mm of 28 days from 1.74 mm of 7 days, with a decreasing trend, which is mainly related to the rate of the cement hydration. In the early stage, the cement hydrates fast, and the pore structure thereof also changes rapidly. However, the closer to 28-day the age is, the slower the hydration rate is.

The method of assessing the drying depth of cementitious material provided by the embodiment of the present invention takes the influence of the resistivity change on the model into consideration, and the drying depth of the cementitious material is derived from the change of the electrochemical parameters, not only increasing the accuracy but also saving much labor, time and cost for testing compared with the existing testing methods. The electrochemical impedance spectrum method provided by the present invention can efficiently reflect the microstructure of the cementitious material specimen. The electrochemical impedance spectroscopy approach is high sensitive, spending less time for testing, and is a non-destructive detecting approach, thereby being a rapid and efficient approach for measuring the drying depth of the cementitious material.

The foregoing is only the preferable embodiment of the present invention, and is not used for limiting the present invention. Any modification, equivalent substitution and improvement made within the spirit and principle of the present invention shall fall within the protection scope of the present invention.

What is claimed is:

1. A method of assessing the drying depth of cementitious material, comprising:
    preparing a plurality of cementitious material specimens;
    drying the cementitious material specimens;
    conducting electrochemical impedance spectroscopy measurement on each cementitious material specimen; and
    accordingly determining a model for analyzing the drying depth of the cementitious material specimen;
    wherein, the step of determining a model for analyzing the drying depth of the cementitious material includes:
        dividing the cementitious material specimen into three parts including, from an outer surface of the specimen, a first part with resistivity rising caused by soaked filter paper and drying (drying influenced), a second part with resistivity decreasing caused by soaked filter paper and drying (drying influenced), and a third part not influenced by drying, wherein the first part and the second part are collectively a drying influenced part;
        dividing the drying influenced part into n elements, in which the first k elements denoted by 1 belongs to the first part, and the following (n−k) elements denoted by 2, from the (k+1)th element to the nth element, belong to the second part, and the third part is denoted by δ;
        wherein, $t_1$ represents the depth of the first part of the cementitious material specimen, $t_2$ is considered to be drying influenced depth of the cementitious material specimen; γ is a constant indicating how sharply the resistivity varies;
    wherein, $\rho_0$ is the resistivity of the outer surface of the cementitious material specimen, $\rho_\delta$ is the resistivity of the third part not influenced by drying, $\rho_1(t)$ is the resistivity of the first part of the specimen at a drying depth of t, and $\rho_2(t)$ is the resistivity of the second part at a drying depth of t; then $\rho_1(t)$ and $\rho_2(t)$ are derived from the following equations, respectively;

$$\rho_1(t) = \rho_\delta \left[ \frac{\rho_\delta}{\rho_0} + \left(1 - \frac{\rho_\delta}{\rho_0}\right)\xi_1^\gamma \right]^{-1}, 0 < t \leq t_1;$$

$$\rho_2(t) = \rho_\delta \left[ \frac{\rho_\delta}{\rho_0} + \left(1 - \frac{\rho_\delta}{\rho_0}\right)\xi_2^\gamma \right]^{-1}, t_1 < t \leq t_2;$$

in which $$\xi_1 = \frac{2t_1 - t}{t_2}, \xi_2 = \frac{t}{t_2}.$$

2. The method of assessing the drying depth of cementitious material according to claim 1, wherein the model for analyzing the drying depth of the cementitious material includes the following equation:

$$Z = 2\sum_{i=1}^{k} \frac{\frac{\rho_1(t_i)t_i}{S}}{1 + [2\pi f \varepsilon_0 \varepsilon \rho_1(t_i)]j} + 2\sum_{i=k+1}^{n} \frac{\frac{\rho_2(t_i)t_i}{S}}{1 + [2\pi f \varepsilon_0 \varepsilon \rho_2(t_i)]j} + \frac{\frac{\rho_\delta(l/2 - t_2)}{S}}{1 + [2\pi f \varepsilon_0 \varepsilon \rho_\delta]j};$$

where Z is an impedance of the entire cementitious material specimen related to frequency; $\varepsilon_0$ is a permittivity of vacuum; ε is a relative dielectric constant of the cementitious material specimen; π is the mathematic constant defined as the ratio of circumference to its diameter, S is a cross sectional area of the cementitious material specimen, l is a length of the cementitious material specimen, and j is an imaginary unit.

3. The method of assessing the drying depth of cementitious material according to claim 1, wherein the step of preparing the cementitious material specimen comprises:
    preparing a cubical cementitious material specimen having a dimension of 30×30×30 mm$^3$, a water-to-cement ratio of 0.4, and a mass ratio of cement to sand of 1:1, curing the cementitious material specimen at a temperature of 20±2° C. with a relative humidity greater than 95% for a desired age, to obtain the cementitious material specimen for testing.

4. The method of assessing the drying depth of cementitious material according to claim 3, wherein the sand is ISO standard sand.

5. The method of assessing the drying depth of cementitious material according to claim 3, the desired age is 7 days, 14 days or 28 days.

6. The method of assessing the drying depth of cementitious material according to claim 1, wherein the step of drying the cementitious material specimens comprises:

sealing four sides of the cementitious material specimen with wax, drying the cementitious material specimen for 1, 4, 24 or 48 hours at a constant temperature of 50° C., respectively, and placing the specimen in between two electrodes for conducting the electrochemical impedance spectroscopy measurement on each specimen.

7. The method of assessing the drying depth of cementitious material according to claim 1, wherein the step of drying the cementitious material specimens comprises:
   ethanol-pretreated drying: soaking the cementitious material specimen in ethanol for 24 hours, and then refreshing the ethanol to soak the cementitious material specimens for another 24 hours to stop the hydration of the cementitious material specimens; sealing four sides of the cementitious material specimen with wax, drying the specimens for 1, 4, 24 or 48 hours at a constant temperature of 50° C. respectively, and conducting the electrochemical impedance spectroscopy measurement on each specimen.

8. The method of assessing the drying depth of cementitious material according to claim 1, wherein the step of conducting electrochemical impedance spectroscopy measurement comprises:
   setting EIS parameter with an AC signal as a sine-wave current of 10 mA, and a measuring frequency range of 0.1 Hz~1 MHz;

preparing two electrodes for measuring: preparing two pieces of filter paper each with a size of 30×30 $mm^2$, soaking each filter paper with 1ml saturated calcium hydroxide solution, the two pieces of filter paper being applied to opposite unsealed ends of the cementitious material specimen respectively with each piece of filter paper being sandwiched between the cementitious material specimen and a steel plate, and connecting the steel plates to an electrochemical work station to conduct the measurement.

* * * * *